(12) United States Patent
Dorsett et al.

(10) Patent No.: US 6,670,117 B2
(45) Date of Patent: Dec. 30, 2003

(54) SPECIFICITY IN THE DETECTION OF ANTI-RUBELLA IGM ANTIBODIES

(75) Inventors: Preston H. Dorsett, Memphis, TN (US); Frances I. Byrd, Memphis, TN (US); Robert F. Devlin, Cordova, TN (US)

(73) Assignee: Viral Antigens, Inc., Memphis, TN (US)

( * ) Notice: Subject to any disclaimer, the term of this patent is extended or adjusted under 35 U.S.C. 154(b) by 0 days.

(21) Appl. No.: 09/850,022

(22) Filed: May 7, 2001

(65) Prior Publication Data

US 2001/0055757 A1 Dec. 27, 2001

Related U.S. Application Data

(63) Continuation of application No. 09/203,161, filed on Dec. 1, 1998, now abandoned.

(51) Int. Cl.$^7$ .......................... C12Q 1/70; G01N 33/53; C07K 14/19; C07K 16/08; C07K 16/10; C07K 17/02; A61K 39/20

(52) U.S. Cl. ....................... 435/5; 435/7.1; 435/7.9; 530/388.3; 530/395; 424/219.1

(58) Field of Search .................. 435/5, 7.9, 7.92, 435/7.95, 12, 7.1; 530/324, 325, 326, 350, 388.3, 395; 424/186.1, 219.1

(56) References Cited

U.S. PATENT DOCUMENTS

| | | |
|---|---|---|
| 4,195,074 A | 3/1980 | Safford, Jr. |
| 4,690,819 A | 9/1987 | Sato et al. |
| 4,965,069 A | 10/1990 | Quash et al. |
| 5,164,481 A | 11/1992 | Lacroix et al. |
| 5,298,596 A | 3/1994 | Lacroix et al. |
| 5,300,427 A | 4/1994 | Fabrizi et al. |
| 5,384,073 A | 1/1995 | Shigekawa et al. |
| 5,422,239 A | 6/1995 | Wands et al. |
| 5,427,792 A * | 6/1995 | Zrein et al. ............. 424/219.1 |
| 5,478,753 A | 12/1995 | Wong et al. |
| 5,556,757 A | 9/1996 | Alstyne et al. |
| 5,663,065 A | 9/1997 | Frey et al. |
| 5,698,393 A | 12/1997 | Macioszek et al. |
| 5,874,218 A | 2/1999 | Drolet et al. |

FOREIGN PATENT DOCUMENTS

| | | |
|---|---|---|
| EP | 0 299 673 | 1/1989 |
| WO | WO 93 07298 | 4/1993 |

OTHER PUBLICATIONS

Seppanen et al., Journal of Clinical Microbiology:29/9:1877–1882, 1991.*

Oker–Blom et al., "Rubella Virus Contains One Capsid Protein and Three Envelope Glycoproteins, E1, E2a, and E2b," *Journal of Virology* 46:964–973 (1983).

Bordier, "Phase Separation of Integral Membrane Proteins in Triton X–114 Solution," *Journal of Biological Chemistry* 256:1604–1607 (1981).

Jenum et al., "Improved Diagnosis of Primary *Toxoplasma gondii* Infection in Early Pregnancy by Determination of Antitoxoplasma Immunoglobulin G Avidity," *Journal of Clinical Microbiology* 35:1972–1977 (1997).

Partanen, Paul et al: "Selective reactivity of antibodies to human immunoglobulins F, M and A with rubella virus proteins" J. Clin. Microbiol. (1985), 21(5), 800–2 (Abstract Only) retrieved from STN Database accession No. 103:4695 Data Base Chemabs 'Online! Chemical Abstracts Service, Columbus Ohio, US.

Thomas, H.I. and Morgan–Capner, P, "The avidity of specific IgM detected in primary rubella and reinfection" *Epidemiol. Infect.* 104:489–497 (1990) (Abstract).

van Sommeren, A.P.G. et al. "Purification of rubella virus E1–E2 protein complexes by immunoaffinity chromatography" *J. Virological Methods* 63:37–46 (1997).

Ghadessi et al., *Clinical Chemistry*, 42(6):S188 (1996) (abstract).

Leat et al., *Clinical Chemistry*, 42(6):S116 (1996) (abstract).

Shapiro et al. *Clinical Chemistry*, 30(6):889–893, (1984).

Chanteloup et al. Abstracts of 93$^{rd}$ ASM General Meeting, Sessioin 27:447 (1993).

* cited by examiner

*Primary Examiner*—James Housel
*Assistant Examiner*—Zachariah Lucas
(74) *Attorney, Agent, or Firm*—Howrey Simon Arnold & White, LLP

(57) ABSTRACT

This invention particularly discloses an improved immunoassay method for the specific detection of anti-rubella IgM antibodies. This method employs rubella antigens comprising rubella E1 and E2 envelope glycoproteins substantially free of capsid protein. Use of this antigen composition reduces or eliminates nonspecific protein-protein interactions leading to false positive results. A sample diluent comprising urea can also be used in the process to further reduce the occurrence of nonspecific protein-protein interactions. A diagnostic kit to aid in the detection of anti-rubella IgM antibodies is also disclosed.

16 Claims, No Drawings

SPECIFICITY IN THE DETECTION OF ANTI-RUBELLA IGM ANTIBODIES

This is a continuation of application Ser. No. 09/203,161, filed Dec. 1, 1998 now abandoned.

FIELD OF THE INVENTION

Improved methods for the specific detection of anti-rubella IgM antibodies in biological samples are disclosed.

BACKGROUND OF THE INVENTION

The rubella virion is a member of the Togavirus family, and is a spherical, enveloped virus approximately 60 nm in diameter. The virion consists of a 10 kb single-stranded RNA molecule encapsidated in an icosahedral nucleocapsid and surrounded by a lipid envelope. Multiple copies of a capsid (C) protein make up the nucleocapsid. The envelope consists of lipoproteins derived from the infected host cell and two viral glycoproteins, designated E1 (53–58 kDa) and E2 (42–48 kDa) (Waxham and Wolinsky, *Virology* 143:153–165, 1985).

Primary rubella infection is characterized in most individuals by the presence of a macropapular rash, fever, malaise, and lymphadenopathy. Rubella is typically a mild and self-limited disease, and is most often contracted during childhood. Primary infection in adults is less common, and may have very serious consequences in pregnant women. Infection of a fetus during the first trimester of pregnancy may result in spontaneous abortion or severe fetal abnormalities. A congenitally infected infant may exhibit one or more of a variety of birth defects collectively known as congenital rubella syndrome (CRS). Common birth defects associated with CRS include cataracts, central nervous system deficits, microcephaly, motor deficits, deafness, congenital heart disease, and mental retardation.

Because of the fetal risk associated with primary maternal rubella infection, test samples from pregnant women are routinely screened for the presence of anti-rubella IgM antibodies during the first trimester of pregnancy. Primary rubella infection is associated with a pronounced specific IgM antibody response, while reinfection (often asymptomatic) is characterized by elevated levels of specific IgG antibodies in the absence of detectable levels of specific IgM antibodies. Unlike primary infection, reinfection of immune pregnant women is generally thought to be harmless to the developing fetus. When prenatal screening indicates that a woman has acquired a primary rubella infection during the early stages of pregnancy, a therapeutic abortion is often recommended. As a result, it is imperative that the test results are accurate.

A variety of methods related to the detection of anti-rubella IgM antibodies have been described. Initial assays relied on hemagglutination inhibition (HAI) testing, which is dependent upon the hemagglutinating properties of the viral E1 and E2 glycoproteins. If a biological sample to be tested contains antibodies directed against these viral hemagglutinins, rubella virus can no longer bind to red blood cells (usually from chicken blood) and this inhibits hemagglutination (see e.g. Peetennans and Huygelen, *Presse Med.* 75:2177–2178, 1967). Unfortunately, titers of these anti-hemagglutinin antibodies increase significantly following both primary infection and reinfection, and so this method cannot be used to distinguish between maternal infections likely to result in fetal defects and maternal infections unlikely to affect the fetus.

More recently, enzyme-linked immunosorbent assays (ELISAs) have become the method of choice in the diagnosis of primary rubella infection (see e.g. Steece et al., *J. Clin. Microbiol.* 21(1):140–142, 1985). In most cases, rubella viral capsid or envelope glycoprotein antigens (whole proteins, viral extracts, or peptides) are immobilized on a solid support and exposed to a biological sample to be tested for the presence of anti-rubella antibodies. Antigens previously described include novel linear and cyclic peptides corresponding to regions of the rubella E1 and C proteins (U.S. Pat. Nos. 5,164,481 and 5,298,596), novel linear and cyclic peptides corresponding to regions of the E1 and E2 glycoproteins (U.S. Pat. No. 5,427,792) and intact rubella virus (or antigens or fragments thereof) in which oligosaccharide moieties have been modified for better recognition by antibodies (U.S. Pat. No. 4,965,069). Any anti-rubella antibodies present in the test sample bind to the immobilized antigen. After appropriate washing, the presence or absence of bound antibody is detected through the use of an indicator reagent capable of complexing with an anti-rubella IgM antibody. This indicator reagent is typically conjugated to a detectable label. After washing, the bound detectable label is quantified directly or indirectly, and the result is used to determine whether or not the initial sample contained specific anti-rubella IgM antibodies. The presence of specific anti-rubella IgM antibodies in a sample forms the basis for a diagnosis of primary rubella infection.

Unfortunately, there is a disturbing lack of specificity in existing anti-rubella IgM immunoassays. False positive results are obtained so frequently that most laboratories use a complicated testing algorithm to confirm an occurrence of primary rubella infection. This algorithm includes repeated testing of each sample employing different anti-rubella IgM diagnostic kits, a time-consuming and expensive process. The algorithm may also include complementary testing for specific anti-rubella IgG antibody avidity. The initial immune response following exposure to a novel antigen is characterized by the production of an abundance of IgM antibodies, whereas the specific high-avidity IgG antibody response is characteristic of secondary responses and reinfection. Consequently, if IgG antibodies from a patient sample taken during early pregnancy bind to rubella antigens with high avidity, it is unlikely that the initial maternal infection occurred during the critical early stages of fetal development. Conversely, if the IgG antibodies in the patient sample bind the antigen with low avidity, it is suggestive of a recent primary infection with the rubella virus.

Several potential causative factors have been implicated in the lack of specificity in anti-rubella IgM immunoassays, and attempts have previously been made to reduce the incidence of false positive assay results. For example, Macioszek et al. (U.S. Pat. No. 5,698,393, issued Dec. 16, 1997; "Macioszek") disclose a method for reducing or eliminating false positive IgM immunoassay results caused by the presence of rheumatoid factors (autoantibodies against human IgG, usually of the IgM isotype) in tested samples. This method involves treatment of samples suspected of containing rheumatoid factors (RF), either directly or while in complex bound to the solid phase, with a RF neutralization citrate buffer of a pH most preferably between 3.5 and 5.0. Macioszek teaches that the binding of nonspecific IgM molecules such as RFs to anti-rubella IgG molecules captured by the affixed antigen is typically disrupted within this pH range, while binding of specific IgM antibodies to immobilized rubella antigen is not disrupted. This patent does not address the problem of assay nonspecificity resulting from the presence of causative factors other than RF, and RF are only present in a subset of tested sera.

Fabrizi et al. (U.S. Pat. No. 5,300,427, issued Apr. 5, 1994; "Fabrizi") also disclose a method for reducing nonspecific signal generated in IgM ELISAs. Examples include an assay for IgM molecules recognizing "extractive antigens" of rubella. This method comprises dilution of serum with buffer containing type IV collagenase prior to placing the serum in contact with the solid support, upon which is affixed anti-IgM antibodies. The complement system is composed of a set of plasma proteins that attack extracellular pathogens. One of these complement proteins, C1q, which is capable of binding serum IgM antibodies, allegedly interacts nonspecifically with the enzyme-conjugated secondary antibody. Fabrizi teaches that collagenase aids in the separation of serum IgM molecules from attached C1q complement molecules, and thereby improves the specificity of the immunoassay by eliminating false positive signals resulting from the abovementioned nonspecific interaction. This patent does not address the problem of assay nonspecificity resulting from the presence of factors other than crossreactive C1q protein in the biological sample.

There exists a need for an improved immunoassay for the detection of anti-rubella IgM antibodies which eliminates all or most of the false positive results generated by current assays without affecting the sensitivity of the assay.

SUMMARY OF THE INVENTION

In a preferred embodiment, the present invention provides improved immunoassays for the detection of anti-rubella IgM antibodies. These assays comprise contacting a test sample suspected of containing anti-rubella IgM antibodies with rubella antigens comprising rubella E1 and E2 glycoproteins substantially free of rubella capsid protein. The present inventor has found that rubella capsid protein may be involved in nonspecific protein-protein interactions leading to false positive assay results.

These assays may further comprise the use of urea in sample diluent. Urea incorporation may further reduce nonspecific binding of IgM molecules to the rubella E1 and E2 glycoproteins used as antigen in the improved immunoassay, thereby farther reducing the incidence of false positive assay results.

In additional preferred embodiments, kits and compositions are provided to facilitate performance of the disclosed immunoassays.

DEFINITIONS

The following definitions are provided in order to aid those skilled in the art in understanding the detailed description of the present invention.

"Agglutination" refers to the clumping together of particles, usually by antibody molecules binding to antigens on the surfaces of adjacent particles.

"Antibody" refers to a protein which binds specifically to a given antigen and is produced in response to initial contact with that antigen.

"Antigen" refers to a molecule or discrete segment thereof capable of eliciting an immune response, wherein the immune response results in the production of antibodies reactive with the antigenic epitope.

"Avidity" refers to the sum total of the strength of binding of two molecules to each other.

"Binary complex" refers to a complex of antigen and IgM, for example, a) the rubella E1 glycoprotein and an anti-rubella IgM antibody specifically recognizing the E1 glycoprotein; b) the rubella E2 glycoprotein and an anti-rubella IgM antibody specifically recognizing the E2 glycoprotein; or c) a combination of E1 and E2 and IgM.

"Cloud point" refers to the temperature at which sudden turbidity appears during warming of a clear micellar detergent solution, the result of a microscopic phase separation.

"Detectable label" refers to molecule, protein, or nucleic acid which may be detected either directly or indirectly through the use of a suitable detection agent or detection device.

"Detection agent" refers to a composition providing conditions suitable for detecting a detectable label. Such compositions often allow the observation of a colorimetric, fluorescent, or chemiluminescent signal when the detectable label is contacted with the detection agent.

"IgM" refers to the antibody isotype characteristic of the primary antibody response following initial exposure to a given antigen.

"IgG" refers to the dominant serum immunoglobulin isotype, which is characteristically produced in secondary phases of the initial infection and in subsequent reinfections.

"Indicator reagent" refers to a molecule, protein, or nucleic acid capable of complexing with an anti-rubella IgM antibody. The binding component may be conjugated to a detectable label.

"Hemagglutination" refers to agglutination of red blood cells.

"Rubella E1 and E2 envelope glycoproteins substantially free of rubella capsid protein" refers to a preparation of rubella envelope glycoproteins, in which no capsid protein is detectable when the preparation is subjected to SDS-PAGE followed by silver staining.

"Ternary complex" refers to a complex of antigen, IgM and indicator reagent, for example, a) the E1 glycoprotein, an anti-rubella IgM antibody specifically recognizing the E1 glycoprotein, and an indicator reagent; b) the E2 glycoprotein, an anti-rubella IgM antibody specifically recognizing the E2 glycoprotein, and an indicator reagent; or c) E1 and E2 in combination with IgM and an indicator reagent.

DETAILED DESCRIPTION OF PREFERRED EMBODIMENTS

Biological samples to be tested by the instant assay are contacted with rubella E1 and E2 envelope glycoproteins substantially free of rubella capsid protein, as Western blots performed by the instant inventors suggest that some of the false positive results generated in other assays may result from nonspecific binding of IgM molecules to the rubella capsid protein. The assays of the instant invention may further comprise addition of urea to sample diluent, in order to further reduce the incidence of nonspecific protein-protein interactions leading to false positive assay results. The method of the instant improved immunoassay typically comprises several steps, as outlined below.

Formation of a Binary Complex

A test sample suspected of containing anti-rubella IgM antibodies is provided. The test sample is contacted with rubella antigens comprising rubella E1 and E2 envelope glycoproteins substantially free of rubella capsid protein. This results in the formation of a binary complex comprising a) the E1 glycoprotein and an anti-rubella IgM antibody specific for the E1 glycoprotein; b) the E2 glycoprotein and an anti-rubella IgM antibody specific for the E2 glycoprotein; or c) a combination of E1 and E2 bound to IgM. The binary complex can be washed several times to effectively remove any uncomplexed material.

Formation of a Labeled Ternary Complex The binary complex is then contacted with an indicator reagent. The indicator reagent typically comprises a binding molecule capable of complexing with an anti-rubella IgM antibody. This results in the formation of a ternary complex comprising a) the E1 glycoprotein, an anti-rubella IgM antibody specific for the E1 glycoprotein, and the indicator reagent; b) the E2 glycoprotein, an anti-rubella IgM antibody specific for the E2 glycoprotein, and the indicator reagent; or c) E1 and E2 bound to IgM and indicator reagent. The indicator reagent is generally conjugated to a detectable label. This ternary complex can be washed several times to remove any uncomplexed material. The ternary complex will preferably be washed prior to the detection step.

Formation of a Labeled Ternary Complex in a Single Step

Alternatively, the test sample can be contacted with rubella E1 and E2 envelope glycoproteins substantially free of rubella capsid protein and the indicator reagent in a single simultaneous step. A ternary complex (as described above) may form. A complex formed in this manner can be washed to remove uncomplexed material. The ternary complex will preferably be washed prior to the detection step.

Detection and Diagnosis

The ternary complexes can be detected either directly or with a suitable detection agent. The particular detection agent selected will depend on the type of detectable label used. A positive signal indicates the presence of anti-rubella IgM antibodies in the test sample, thereby suggesting that the individual providing the test sample may have recently acquired a primary rubella infection. Conversely, the absence of a signal indicates the absence of anti-rubella IgM antibodies in the test sample.

The organism providing the test sample is generally any organism which contains antibodies. The organism preferably is a mammal, and more preferably is a human.

The test sample can generally be any biological material containing antibodies. Such materials can be processed so that they are provided in a suitable form. The test sample is preferably provided from a bodily fluid, more preferably is provided from blood, and most preferably is provided from serum.

The test sample can be diluted with a sample diluent, which can comprise urea ($N_2H_4CO$). The incorporation of urea, a compound with chaotropic activity, reduces the nonspecific binding of IgM to the abovementioned E1 and E2 envelope glycoproteins and/or a solid phase support material used in the assay. The urea increases the stringency of the antibody:antigen interaction, with the effect that low-avidity complexes resulting in false positive assay results are excluded. Such low avidity complexes can be composed of nonspecific IgM molecules that have bound to cross-reactive epitopes on the rubella E1 or E2 glycoproteins. Preferably, the sample diluent will comprise between about 1 M and about 5 M urea, more preferably between about 2 M and 4 M urea, and most preferably about 3 M urea.

The wash buffer used to wash the bound binary and/or ternary complexes described above can comprise urea. The wash buffer will preferably comprise about 1 M urea to about 5 M urea. More preferably, the wash buffer will comprise about 2 M urea to about 4 M urea, and most preferably about 3 M urea. One of ordinary skill in the art is aware that these wash buffers may otherwise vary in their composition, but still be compatible with the present invention.

The rubella E1 and E2 envelope glycoproteins substantially free of rubella capsid protein can be prepared from any strain of rubella virus, including the Therien, Judith, M33 and $HPV_{77}$ strains. These E1 and E2 envelope glycoproteins can be purified from capsid protein by any method compatible with the assay of the instant invention. Preferably, these glycoproteins will be purified away from capsid protein through phase separation into detergent micelles, and most preferably, these glycoproteins will be purified according to the method described in Example 1. It will be recognized by those of skill in the art that changes can be made in the specific method described while still obtaining a like or similar result and without departing from the spirit and scope of the disclosed method. Alternatively, rubella E1 and E2 glycoproteins substantially free of rubella capsid protein can also be obtained by other methods well known to those of skill in the art, including alternative purification methodologies, translation in in vitro translation systems, and expression in bacteria, yeast, CHO cells, insect cells, or other cell systems. All such variations are considered equivalent for the purposes of the present invention.

The E1 and E2 viral glycoproteins substantially free of rubella capsid protein can be immobilized on a solid support. The solid support can be provided in one of many different forms. Representative examples of solid support materials include membranes, filters, glass, plastic, plastic beads, agarose beads, SEPHAROSE® (polysaceharide) beads (SEPHAROSE® is a registered trademark of Pharmacia Biotech, Piscataway, N.J.), and magnetic beads.

In addition to the different forms, the solid support can be composed of a variety of materials. The solid support is preferably nitrocellulose, polyvinylidene difluoride, nylon, rayon, cellulose acetate, agarose, SEPHAROSE® (polysaccharide) beads, metal, polypropylene, polyethylene, polystyrene, polyvinyl chloride, polyvinyl acetate, polyamide, polyimide, polycarbonate, polyether, polyester, polysulfone, polyacetal, polystyrene, or polymethyl methacrylate; more preferably is polypropylene, polystyrene, polyvinyl chloride, polyamide, polycarbonate, polyether, polymethyl methacrylate, nitrocellulose, polyvinylidene difluoride, or nylon; and most preferably is polypropylene or polystyrene.

The indicator reagent is typically conjugated to a detectable label. The detectable label can be an enzyme, such as alkaline phosphatase, β-galactosidase, or peroxidase; a protein, such as biotin or digoxin; a fluorochrome, such as rhodamine, phycoerythrin, or fluorescein; a fluorescent protein such as GFP or one of its many modified forms; a radioisotope; or a nucleic acid segment.

Some of these detectable labels can be detected directly. Fluorochromes (Wells and Johnson. In *Three-Dimensional Confocal Microscopy*, pp. 101–129, 1994) and fluorescent proteins (Sakai et al., *J. Cell Biol.* 139(6):1465–1476, 1997) can be directly detected with a suitable detection device, such as a fluorescent microscope, fluorescent activated cell sorter (FACS), or fluorometer. Radioisotopes (such as $^{32}P$ or $^{125}I$) can be detected through the use of a scintillation counter or Geiger counter.

Other labels can be detected indirectly. These labels may require the use of a suitable detection agent. The choice of a suitable detection agent generally depends on which detectable label is used.

For example, if a protein such as biotin is used as the detectable label, a detection agent comprising avidin or streptavidin is generally employed (Bayer et al., *Meth. Biochem. Anal.* 26: 1–10, 1980). In such cases, a suitable detection agent generally comprises a binding component capable of complexing with the protein. This binding component can be further detected by contacting it with a second detectable label.

Enzymes, such as horseradish peroxidase, alkaline phosphatase, and β-galactosidase, can also be used as detectable labels. Detection agents for enzymes generally utilize a form of the enzyme's substrate. The substrate is typically modified, or provided under a set of conditions, such that a chemiluminescent, calorimetric, or fluorescent signal is observed after the enzyme and substrate have been contacted (Vargas et al., *Anal. Biochem.* 209: 323, 1993).

Nucleic acids, when used as detectable labels, can be detected through the use of a hybridizing probe. This probe can be conjugated to an additional detectable label which, when placed under suitable conditions, provides a fluorescent, chemiluminescent, calorimetric, or radioactive signal. Alternatively, the nucleic acid can be amplified by means of a polymerase chain reaction (PCR) (Dirks et al.,*J. Histochem. Cytochem.* 38:467–476, 1990). The amplified nucleic acid can be easily detected by gel electrophoresis.

Radioisotopes can alternatively be detected indirectly by autoradiography (i.e. exposure to x-ray film).

There are many other suitable detection methods compatible with the instant invention. In each case, the detection agent and its method of use are well known to one of ordinary skill in the art.

A diagnostic kit can be designed to aid in the performance of the above method. Such a kit can contain vessels containing rubella E1 and E2 envelope glycoproteins substantially free of rubella capsid protein and the indicator reagent, respectively. The kit can further contain test sample diluent, various blocking buffers, buffers to aid the formation of binary and ternary complexes, wash buffers, and detection agents. One of ordinary skill in the art is aware that the diluent and buffers can vary in their exact composition, but still be compatible with the present invention. All such variations are considered equivalent for the purposes of the present invention. The test sample diluent and/or wash buffers can comprise urea, as described above.

The rubella E1 and E2 envelope glycoproteins substantially free of rubella capsid protein supplied in the diagnostic kit can be purified as described above from any strain of rubella virus.

The E1 and E2 viral glycoproteins substantially free of rubella capsid protein supplied in the diagnostic kit can be provided already immobilized on a solid support. This solid support can be provided in one of many different forms, and be composed of a variety of materials, as described above.

The diagnostic kit can further comprise a detection agent. As previously mentioned, the choice of a suitable detection agent generally depends on which detectable label is used. Many different detectable labels and detection agents are compatible with the present invention.

The components of the diagnostic kit can be provided in many different forms and quantities. Various types of packaging can also be used. Instructions for the correct use of the kit can be supplied with the kit. Any such alternative embodiments are considered equivalent to the present invention.

In a further preferred embodiment, the invention relates to a composition comprising rubella E1 and E2 envelope glycoproteins substantially free of rubella capsid protein, as described above.

In yet another preferred embodiment, the invention relates to a solid support material having immobilized thereon rubella E1 and E2 envelope glycoproteins substantially free of rubella capsid protein. The rubella E1 and E2 glycoproteins substantially free of rubella capsid protein can be prepared according to any of the methods described above, and can be affixed to any of the solid support materials previously described.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of Rubella Virus Glycoproteins

Partially purified or highly purified rubella virus in buffer containing 150 mM NaCl, 10 mM Tris-HCl (pH 8.15), 10 mM EDTA, and 1.0 M KCl (NTE/KCl) was adjusted to 0.1 to 1.0 mg/mL protein by dilution in the same NTE/KCl buffer. TRITON™ X-114 surfactant (TRITON™ is a registered trademark of Rohm and Hans Co., Spring House, Pa.) was then added to a final concentration of 1% (vol/vol). The solution was placed in an ice-water bath for 30 minutes and mixed at intervals by vortexing, after which it was allowed to incubate at room temperature for 10 to 15 minutes. As the solution warmed, it became turbid due to a microscopic phase separation that occurred when the solution temperature passed the cloud point. During the room temperature incubation the solution was mixed vigorously two times by vortexing for 30 to 60 seconds to maximize the interaction of the glycoproteins with the forming micelles. The solution was then centrifuged for 10 minutes at 1000 ×g at room temperature to collect the detergent phase at the bottom of the tube. The upper aqueous phase, containing the capsid protein, was removed and the detergent phase was solubilized in the original volume of cold NTE/KCl. After a few minutes in the ice-water bath, the temperature of the solubilized detergent phase was allowed to rise above the cloud point with mixing, thereby allowing phase separation to occur as described above. The detergent phase was collected and solubilized and the phase separation was repeated twice. After the third phase separation, the detergent phase containing the glycoproteins was solubilized in one-half the original volume of cold NTE buffer. The detergent was removed by three extractions with cold ether, after which the rubella virus glycoproteins were in the aqueous phase. Capsid protein was not detectable as an impurity in the extracted glycoproteins, as demonstrated by SDS-PAGE followed by silver staining.

Example 2

Preparation of the Solid Support Material

The rubella virus glycoproteins were assayed in an antigen-dilution IgM ELISA to determine the optimal antigen concentration for sensitization of the solid phase. The glycoprotein solution was diluted in bicarbonate-carbonate buffer, pH 9.5, to within the range of 0.1 mcg/ml to 10 mcg/ml, typically 1 mcg/ml, and 0.1 mL was placed in each well of a 96-well microtiter plate. The plates were incubated at 4–7° C. overnight to allow the glycoproteins to adsorb to the plastic surface. After adsorption, the fluid was removed from the plate wells. A blocking solution of phosphate buffered saline, pH 7.0 containing 1% w/v bovine serum albumin and 5% w/v sucrose (0.2 mL) was then added to each well and the plates were incubated overnight at 4–7° C. The blocking solution contained proteins that adsorb to the remaining sites on the plastic wells and help block subsequent adsorption of the test serum globulins to the plastic surface. After blocking, the fluid was removed from the plate wells and the plates were allowed to air dry. The plates were then sealed in a foil pouch along with a dessicant bag.

Example 3

Preparation of the IgM Serum Diluent

The serum diluent for the IgM ELISA consisted of phosphate buffered saline containing 1 M KCl, goat antihuman IgG (Fc specific) and 3 M urea. The goat antihuman IgG obtained from DiaSorin, Stillwater, Minnesota, was first cross species adsorbed with bovine gamma globulin, rabbit gamma globulin, etc. and was adjusted in concentration to precipitate human IgG in a range from 5 to 20 mg/mL.

Example 4

Method for Performing an IgM ELISA

The serum test samples, an IgM calibrator serum and an IgM positive control serum were individually diluted 1:10 or greater in the IgM serum diluent of Example 3. The dilutions were allowed to incubate at room temperature for 10 to 60 minutes, after which 0.1 mL of each diluted serum was placed in a separate well of the antigen-coated plate described in Example 2. After addition of all the serum samples, the plate was incubated in a moist chamber at room temperature for 30 minutes. The fluid was removed by inverting the plate over a sink or beaker and then slapping the plate on paper towels to remove any excess diluted serum. Each well was washed three times with a wash buffer consisting of phosphate buffered saline containing 0.1% (wt/vol) bovine serum albumin and 0.05% (vol/vol) TWEEN™-20 detergent (TWEEN™ is a registered trademark of Robin and Haas Co., Spring House, Pa.). The wells were filled with wash buffer and the fluid was removed as described above. After the final wash was removed from the wells, 0.1 mL of goat antihuman IgM conjugated with alkaline phosphatase obtained from Kirkegaard and Perry Laboratories, Inc., Gaithersburg, Md. (IgM conjugate) was placed in each well. The IgM conjugate was diluted in phosphate buffered saline containing 1% (wt/vol) bovine serum albumin and 0.05% TWEEN™-20 detergent prior to use. The conjugate was allowed to incubate for 30 minutes at room temperature in a moist chamber. After incubation, the conjugate was removed from the wells, and each well was washed 3 times with wash buffer as described above. After the last wash was removed from the wells, 0.1 mL of alkaline phosphatase substrate solution was placed in each well, and the plate was incubated for 30 minutes at room temperature in a moist chamber to allow color development. The color was read at 405 nm using a spectrophotometer.

The test absorbance values were converted to Relative ELISA Values (REV) by expressing the test serum absorbance value as a ratio of the absorbance of the calibrator serum. This was performed as follows:

(i) obtain the absorbance value for the blank well(s) containing everything but the serum;
(ii) obtain absorbance values for test and calibrator samples;
(iii) subtract the blank absorbance value from each of the test and calibrator sample values to obtain corrected values;
(iv) multiply the calibrator absorbance by the calibration factor (calibration factor is the factor by which the calibrator [a low positive serum] absorbance must be multiplied to reach the cut-off point, which is three standard deviations above the mean negative absorbance of a population) indicated on the calibration serum to obtain the ELISA cutoff value; and
(v) divide the corrected absorbance for each test serum by the cutoff value to obtain the REVs. REVs equal to or greater than 1.0 are considered positive for IgM antibodies against rubella virus, while those below 1.0 are considered negative.

Example 5

Comparative Studies of Assay Accuracy

A panel of 102 serum samples that were known negative for IgM antibodies and 25 serum samples that were known positive for IgM antibodies were assayed by the methods of the instant invention. The same sera were assayed with a commercially available kit and by a preexisting in-house ELISA, both of which employed detergent-disrupted purified virus as the antigen and a serum diluent lacking urea. All three tests correctly identified the positive sera.

Table I shows that the commercial kit and the preexisting in-house ELISA yielded significant numbers of false positive reactions within the negative serum panel, whereas the ELISA of the instant invention ("New" ELISA) correctly identified all 102 negative samples.

TABLE I

Comparative Assays of 102 Known Negative Samples

| ASSAY | POSITIVE | NEGATIVE |
|---|---|---|
| In-house ELISA | 16 | 86 |
| Commercial Kit | 7 | 95 |
| "New" ELISA | 0 | 102 |

Example 6

"New" ELISA without urea 100 negative serum samples were tested using the ELISA of the instant invention ("New" ELISA) employing rubella E1 and E2 glycoproteins as antigen. Urea was omitted from the sample diluent. No false positive results were obtained, but the relative ELISA values (REVs) ranged from 0 to 0.8, a fairly broad range. Samples yielding REVs of 1.0 or greater (as discussed above) are considered positive for the presence of anti-rubella IgM antibodies. However, approximately 90% of the obtained REVs were 0.2 or less, indicating that use of the E1 and E2 glycoproteins as antigen in immunoassays is very effective in the elimination of false positive results even when no urea is added to the sample diluent.

Example 7

"New" ELISA with urea

The same 100 negative serum samples were tested using the ELISA of the instant invention ("New" ELISA) employing E1 and E2 glycoprotein as antigen and further employing a sample diluent containing 3 M urea. No false positive results were obtained, and furthermore, the REV distribution was narrowed to a range of 0 to 0.4, with over 95% of the values equal to 0. This indicates that the "New" ELISA using both the E1 and E2 glycoprotein antigens and urea in the sample diluent is superior in sensitivity to the ELISA using only the E1 and E2 glycoprotein antigens.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope, and concept of the invention.

What is claimed is:

1. A method for detecting anti-rubella IgM antibodies, comprising:
   a) providing a test sample suspected of containing anti-rubella IgM antibodies;
   b) contacting the test sample with rubella antigens comprising rubella E1 glycoprotein and rubella E2 glycoprotein and substantially free of rubella capsid protein to form a binary complex, wherein the E1 and E2 glycoproteins are purified from rubella virus and wherein said binary complex is a complex of rubella antigens and IgM;
   c) contacting the binary complex with an indicator reagent to form a ternary complex; and
   d) detecting the presence or absence of the ternary complex; wherein said method specifically detects anti-rubella IgM antibodies and substantially eliminates false positive results.

2. The method of claim 1, wherein the test sample is obtained from a bodily fluid.

3. The method of claim 1, wherein the test sample is obtained from blood.

4. The method of claim 1, wherein the test sample is diluted with a diluent comprising urea prior to contacting the sample with the rubella antigens.

5. The method of claim 4, wherein the diluent comprises between about 2 M urea and about 4 M urea.

6. The method of claim 4, wherein the diluent comprises about 3 M urea.

7. The method of claim 1, further comprising washing the binary complex or ternary complex with a wash comprising urea.

8. The method of claim 7, wherein the wash comprises between about 2 M urea and about 4 M urea.

9. The method of claim 1, wherein the rubella antigens are immobilized on a solid support.

10. The method of claim 9, wherein the solid support is a membrane, filter, piece of plastic, piece of glass, or bead.

11. The method of claim 9, wherein the solid support is polypropylene, polystyrene, polyvinyl chloride, polyamide, polycarbonate, polyether, polymethyl methacrylate, nitrocellulose, polyvinylidene difluoride, agarose, metal, or nylon.

12. The method of claim 1, wherein the indicator reagent is conjugated to a detectable label.

13. The method of claim 12, wherein the detectable label is a protein, enzyme, radioisotope, nucleic acid segment, or fluorochrome.

14. The method of claim 13, wherein the enzyme is horseradish peroxidase, alkaline phosphatase, or β-galactosidase.

15. The method of claim 13, wherein the enzyme catalyzes the conversion of a non-chemiluminescent reagent into a chemiluminescent product.

16. The method of claim 13, wherein the enzyme catalyzes the conversion of a non-colorimetric reagent to a colorimetric product.

* * * * *